United States Patent
Lundgren et al.

(10) Patent No.: US 7,420,678 B2
(45) Date of Patent: Sep. 2, 2008

(54) MULTI-SPECTRAL IMAGING

(75) Inventors: Mark A. Lundgren, Fullerton, CA (US); Edward Stoll, Corona, CA (US)

(73) Assignee: The Boeing Company, Chicago, IL (US)

( * ) Notice: Subject to any disclaimer, the term of this patent is extended or adjusted under 35 U.S.C. 154(b) by 237 days.

(21) Appl. No.: 11/224,353

(22) Filed: Sep. 12, 2005

(65) Prior Publication Data

US 2007/0058921 A1    Mar. 15, 2007

(51) Int. Cl.
G01N 21/25 (2006.01)

(52) U.S. Cl. ............................ 356/419

(58) Field of Classification Search .......... 356/418–419
See application file for complete search history.

(56) References Cited

U.S. PATENT DOCUMENTS

| | | | |
|---|---|---|---|
| 3,861,788 A | | 1/1975 | Webster |
| 3,864,037 A | * | 2/1975 | Johnston ............... 356/418 |
| 5,949,074 A | | 9/1999 | Dombrowski et al. |
| 5,991,099 A | | 11/1999 | Lundgren |
| 6,002,488 A | | 12/1999 | Berg et al. |
| 6,191,860 B1 | * | 2/2001 | Klinger et al. ............... 356/419 |
| 6,813,018 B2 | | 11/2004 | Richman |
| 7,148,967 B1 | * | 12/2006 | Slagle ............... 356/419 |
| 2002/0135770 A1 | * | 9/2002 | Lewis et al. ............... 356/419 |
| 2003/0227674 A1 | * | 12/2003 | Nihoshi et al. ............... 359/386 |
| 2004/0264796 A1 | | 12/2004 | Turner et al. |
| 2005/0180634 A1 | * | 8/2005 | Berman et al. ............... 382/191 |
| 2006/0269215 A1 | | 11/2006 | Lundgren |

OTHER PUBLICATIONS

Di-Yuan Tzeng et al., "Spectral-Based Ink Selection for Multiple-Ink Printing I. Colorant Extimation . . . ", Rochester Institute of Technology, Rochester, NY.
"Multispectral Imaging in Food and Agriculture", Hi-Tech Electronics Pte Ltd.
K. Kim Luu et al., "Object Characterization From Spectral Data".
Kira Jorgensen et al. "Most Recent Findings From the NASA AMOS Spectral Study (NASS): Squiggley Lines Lead to Physical Properties of Orbiting Objects".

(Continued)

*Primary Examiner*—Kara E Geisel
(74) *Attorney, Agent, or Firm*—MacPherson Kwok Chen & Heid LLP; Brent A. Folsom

(57) ABSTRACT

Systems and techniques for multi-spectral imaging. Light may be received at a multi-spectral optical module, which transmits a plurality of wavelength band portions of the received light, each having a pre-selected bandwidth between about two nanometers and about forty nanometers. The pre-selected bandwidths may be between about ten nanometers and about thirty nanometers. Each of the wavelength band portions may have the same pre-selected bandwidth, or may have different pre-selected bandwidths.

17 Claims, 6 Drawing Sheets

OTHER PUBLICATIONS

Dennis W. Morelli, "Variable Filters", OCLI-Optical Coating Laboratory, Inc.

Glenn Healey et al. "Models and Methods for Automated Material Identification in Hyperspectral Imagery Acquired . . . ", IEEE 1999.

Sofya Poger et al. "Multispectral Sensors in Computer Vision", Stevens Institute of Technology, Department of Computer Science.

Correlation and Linear Regression, http://members.tripod.com/~Richard Bowles/maths/correlation/corr.htm, 8 pages no date.

Hillman et al., Compact Imaging Spectrometers using Acousto-Optic Tunable Filters, http://www.stsci.edu/stsci/meetings/space_detectors/hillman.htm, 4 pages no date.

* cited by examiner

MULTI-SPECTRAL IMAGING

BACKGROUND

1. Field of Invention

The present disclosure relates generally to optics, and more particularly to systems and techniques for multi-spectral imaging.

2. Background

For some applications, existing imaging systems are not optimal. For example, in order to accurately determine one or more material characteristics of an object (such as an object in space), existing systems may provide for too much or too little image information. Insufficient image information may not allow accurate determination of material characteristics, while excessive information may require more image processing resources and processing time and thus be inefficient.

One example of a system that may be used to determine material characteristics is a hyper-spectral imaging system. In a hyper-spectral imaging system, an object is imaged at a large number of narrow wavelength bands. The wavelength bands are generally less than about a nanometer in width, so that detailed spectral information about the imaged object is obtained. However, data acquisition and analysis for a hyper-spectral imaging system may be complex and time consuming.

Another example of a system that may be used to determine material characteristics is a television (TV) 3-color measurement system. In a TV system, information is obtained in three color bands; red, green, and blue. TV 3-color imaging is fast and generally inexpensive. However, the information obtained is limited to three broad color bands. Thus, it may be difficult to accurately identify material properties based on image information obtained using a TV 3-color imaging system.

SUMMARY

In general, in one aspect, a multi-spectral imaging system comprises an image acquisition system and a multi-spectral optical module. The multi-spectral optical module may be configured to receive light and to sequentially transmit to the image acquisition system a plurality of wavelength bands having a pre-selected bandwidth of between about two nanometers and about forty nanometers. In some embodiments, the pre-selected bandwidth may be between about ten nanometers and about thirty nanometers.

The system may further comprise a controller configured to control the multi-spectral optical module to couple each of the plurality of wavelength bands to the image acquisition system in turn.

The multi-spectral optical module may comprise a filter configured to filter the received light based on wavelength, and may further comprise a light formatter to format the received light to transmit substantially one dimensional light to the image acquisition system. The light formatter may comprise a light blocker including an aperture. The filter may be a linear filter, such as a linear variable filter or angular variable filter. The multi-spectral optical module may be configured to transmit a particular one of the plurality of wavelength bands based on a relative position of a first part of the multi-spectral optical module with respect to a second part of the multi-spectral optical module.

In general, in another aspect, a method may comprise receiving light from an object comprising one or more materials at a multi-spectral optical module. At the multi-spectral optical module, a plurality of wavelength band portions of the received light may be transmitted, wherein the wavelength band portions each have a pre-selected bandwidth between about two nanometers and about forty nanometers. Transmitting each of the portions may comprise configuring the multi-spectral optical module to transmit light included in the associated wavelength band portion of the received light to an image acquisition system, and to exclude light outside the associated wavelength band portion. The method may further comprise receiving the wavelength band portions at the image acquisition system and generating image data corresponding to each of the wavelength band portions. The method may further comprise processing at least some of the image data and identifying at least one material of the one or more materials based on the processing of at least some of the image data. The method may further comprise receiving light at a first reflection angle, and subsequently receiving light at a second different reflection angle.

In general, in another aspect, an article comprising a machine-readable medium embodying information indicative of instructions that when performed by one or more machines result in operations comprising receiving image data indicative of an optical response of a plurality of materials of an object in a plurality of wavelength bands each having a pre-selected bandwidth in the range from about two nm to about forty nm, wherein the image data comprises image data for a plurality of image pixels.

The operations may further comprise comparing the image data to reference data corresponding to a plurality of candidate materials, the reference data comprising data indicative of an optical response of each of the candidate materials for the plurality of wavelength bands. The operations may further comprise determining an identity of a first material of the plurality of materials corresponding to a first image pixel of the plurality of image pixels based on the comparing, and determining an identity of a second material of the plurality of materials corresponding to a second image pixel of the plurality of image pixels based on the comparing.

These and other features and advantages of the present invention will be more readily apparent from the detailed description of the exemplary implementations set forth below taken in conjunction with the accompanying drawings.

BRIEF DESCRIPTION OF THE DRAWINGS

Like reference symbols in the various drawings indicate like elements.

DETAILED DESCRIPTION

As noted above, some existing imaging systems may provide too much or too little data to efficiently and accurately identify desired material parameters. For example, existing systems may not be optimal for determining material properties of one or more objects.

Figure 1A:
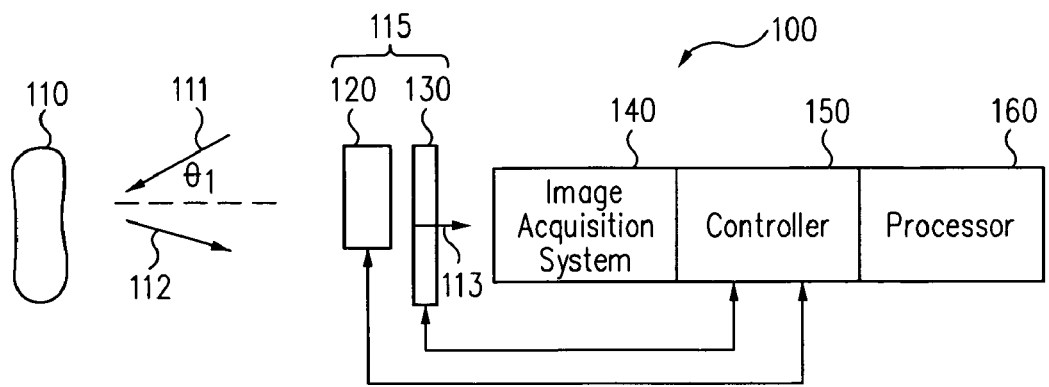
FIG. 1A is a schematic side view of an imaging system, according to some embodiments.

Systems and techniques described herein may provide more efficient optical imaging and analysis, for some applications. FIG. 1A shows an implementation of a system 100, according to some implementations. System 100 utilizes multi-spectral imaging techniques to efficiently determine a distribution of one or more material properties of an object 110. For example, system 100 may be used to identify the spatial distribution of different materials on the surface of the imaged object.

In operation, light 111 is incident at an angle $\theta_1$ to a surface normal of an object 110 to be imaged. Light 112 from object 110 is incident on a multi-spectral optical module 115. Multi-spectral optical module 115 includes components configured to modify incoming light of a broad spectrum to provide a plurality of wavelength bands to an image acquisition system 140. Each of the wavelength bands may have a width of about 2 nm to about 40 nm. In some implementations, the width of the wavelength bands is about 10 nm to about 30 nm.

Module 115 accepts broadband light from a two-dimensional scene, and produces a staggered (e.g., time-phased) plurality of output light samples at narrower optical bandwidth, that may be formed into complete two-dimensional images.

In FIG. 1A, multi-spectral optical module 115 includes a filter 120 and a light modifier 130. Filter 120 may be, for example, a linear variable filter or an angular variable (e.g. circular variable) filter. The wavelength of the light that passes through filter 120 varies along the extent (vertical, horizontal, or angular, depending on the configuration used) of filter 120.

Figure 1B:
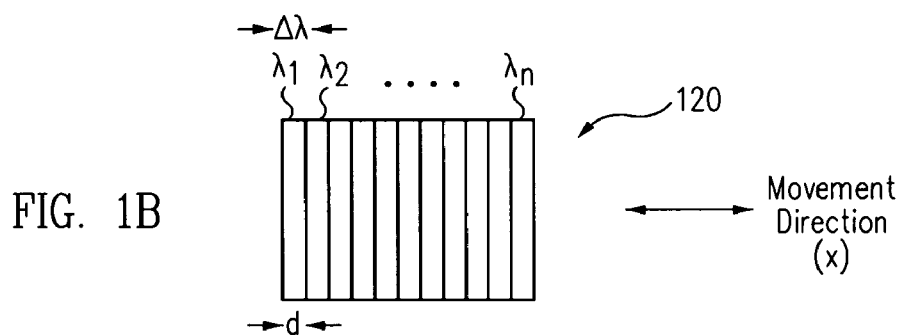
FIG. 1B is a front view of a linear variable filter that may be used with the system of FIG. 1A, according to some embodiments.

FIG. 1B shows a linear variable filter 120 that may be used in some embodiments. In the example of FIG. 1B, the wavelength of light that is passed by the filter varies along the horizontal (x) direction. A band of filter 120 of length d acts as a bandpass filter to pass light having a wavelength band of $\Delta\lambda$, centered about $\lambda_1$. Some examples of linear variable filters include filters supplied by JDSU Uniphase of San Jose, Calif., filters from Ocean Optics of Dunedin, Fla., and filters such as part number R04610-00 from Raynard Corporation of San Clemente, Calif.

Figure 1C:
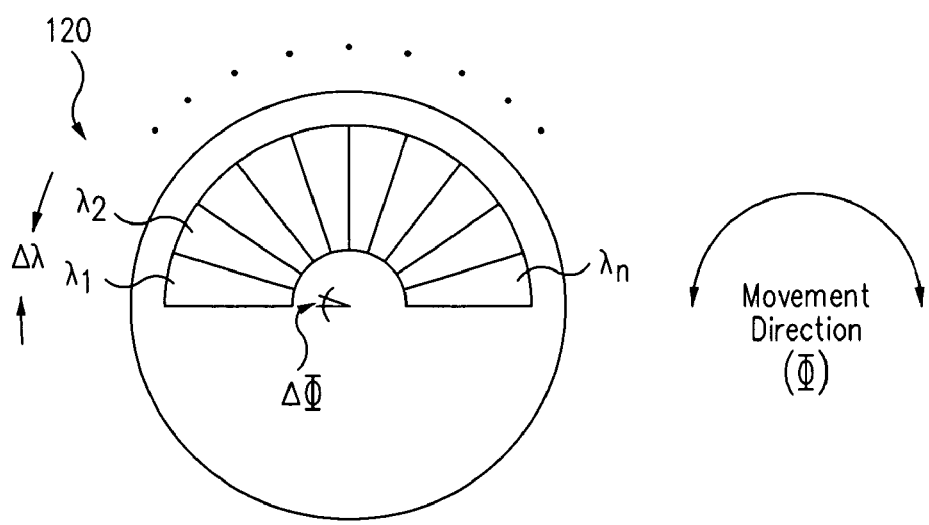
FIG. 1C is a front view of a linear angular filter that may be used with the system of FIG. 1A, according to some embodiments.

FIG. 1C a variable circular filter 120 that may be used in some embodiments. In the example of FIG. 1C, the wavelength of light that is passed by the filter (e.g., $\lambda_1$) varies with the rotation angle $\Phi$. A band of filter 120 corresponding to an angular displacement $\Delta\Phi$ acts as a bandpass filter to pass light having a wavelength band of $\Delta\lambda$, centered about $\lambda_1$. Variable circular filters may be obtained from, for example, OCLI of Santa Rosa, Calif.

In some embodiments, different filter types may be used. For example, liquid crystal electronically tunable filters, variable etalon filters, acousto-optical filters, or other filters. However, other filter types may be relatively heavy or complicated, may have relatively poor efficiency, and/or may have a limited range.

Using variable filters rather than discrete filters (e.g., filters with a plurality of discrete filter elements each configured to pass a particular bandwidth) may provide a number of benefits. For example, pseudo-continuous data may be generated, rather than discrete chunks of data. Additionally, the images may be spaced finer than the bandwidth. For example, for a relatively dim target, the bandwidth may be set somewhat wider than the desired bandwidth (e.g., 10 nm), but images may be acquired at wavelengths differing by an amount less than the bandwidth (e.g., 5 nm). A sort of "running average" is obtained, where the wavelength ranges for consecutive images will overlap to some extent.

Light from filter 120 is incident on a light modifier 130. Light modifier 130 formats received light to alter the spatial profile of the light. Light modifier 130 may include an aperture configured to transmit only a portion of the incident light. Light modifier 130 may be positioned with respect to filter 120 so that the aperture transmits light in a pre-selected narrow wavelength band and substantially blocks light outside the narrow wavelength band.

In other embodiments, light modifier may comprise optical components configured to squeeze the light received by the object (e.g., the light comprising the two dimensional scene) through a narrow band of the filter corresponding to the desired wavelength band. In such an embodiment, substantially all of the received light may be available for processing in system 100. Exemplary systems and techniques are described in commonly assigned U.S. patent application Ser. No. 11/138,782, entitled "Distorted Pupil Relay for Spectral Filtering," filed on May 26, 2005, which is hereby incorporated by reference.

In order to provide sufficient data to accurately identify one or more materials of object 110 relatively quickly, the wavelength bands may be on the order of 10 nm to about 30 nm in width. In some implementations, wider or narrow bands may be used; for example between about 1 or 2 nanometers in width to about 40 nanometers in width may be used. The number of bands is generally between about 10 and 30, although more or fewer may be used. For example, in order to cover the visible spectrum, which spans a wavelength range of about 300 nm, about 10 to 150 wavelength bands may be used.

Obtaining data for large numbers of wavelength bands may require significant time and processing resources. Therefore, in some embodiments, smaller wavelength bands may be used for a portion of the spectrum (e.g., for a 50 nm wide portion of the about 300 nm wide visible spectrum). Note that the data need not be confined to the visible spectrum. For example, image acquisition system 140 may comprise charge coupled device (CCD) or CCD-like imagers, image intensifier tubes, or other apparatus for obtaining image data for wavelengths outside of the visible range (e.g., in the ultraviolet, deep ultraviolet, infrared, and thermal infrared portions of the electromagnetic spectrum).

Figure 1D:
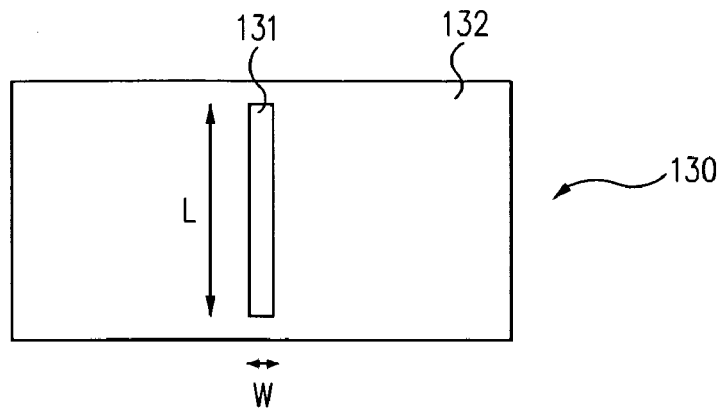
FIG. 1D is a front view of a modifier that may be used with the system of FIG. 1A, according to some embodiments.

FIG. 1D shows a front view of an exemplary embodiment of a modifier 130. Modifier 130 comprises an elongate aperture 131 in a light blocker 132. As shown in FIG. 1B, the elongate aperture 131 is a rectangular slot having a width w. Modifier 130 may be positioned with respect to filter 120 so that a particular wavelength band is transmitted through aperture 131 to image acquisition system 140. Although the light at a receiving plane of optical module 115 is two dimensional, light transmitted to image acquisition system 140 is substantially one-dimensional.

In order to acquire image data at a plurality of wavelength bands of a particular wavelength bandwidth, the relative position of at least one of filter 120 and modifier 130 may be changed. Referring to FIGS. 1B and 1D, filter 120 may initially be positioned so that light from a first filter element configured to filter light having a wavelength band of width $\Delta\lambda$ centered around wavelength $\lambda_1$ is transmitted to image acquisition system 140. Image data corresponding to $\lambda_1$ may be acquired. Filter 120, modifier 130, or both may then be moved so that a different filter element configured to filter light centered around a different wavelength (such as $\lambda_2$) is aligned with aperture 131 of modifier 130, and additional image data acquired. Filter 120 and/or modifier 130 may be moved using, for example, a stepper motor in communication with a stepper motor controller or other controller.

Similarly, referring to FIGS. 1C and 1D, filter 120 may initially be positioned so that light from a first filter element configured to filter light having a wavelength band of width $\Delta\lambda$ centered around wavelength $\lambda_1$ is transmitted to image acquisition system 140. Filter 120 may then be rotated so that light from a different filter element is transmitted to image acquisition system 140. Note that the filter characteristics may vary continuously along the filter, so the phrase "filter element" is defined by the light coupled to the image acquisition system, rather than by features of the filter. Note that in embodiments in which discrete filters are used, filter elements are defined by features of the filter.

System 100 may be configured so that the width of the wavelength band is adjustable. For example, at least one of filter 120 and modifier 130 may be adjustable so that different bandwidths may be coupled into image acquisition system 140. This may be accomplished in a number of ways; for example, by providing an adjustable aperture, by varying the relative position of filter 120 with respect to modifier 130, and the like. Another technique that may be used is to implement a filter comprising a low-pass filter and a high-pass filter. Moving them with respect to one another creates a variable bandpass filter. Variable filter systems incorporating a low-pass filter and a high-pass filter may be obtained from Ocean Optics of Dunedin, Fla.

Image acquisition system 140 may comprise a camera, such as a CCD (charge coupled device) camera, a CMOS (complementary metal oxide semiconductor) camera, and/or other camera. Image acquisition system 140 may comprise an image intensifier, and/or an ultraviolet, visible, or infrared focal plane array. For each wavelength band, system 140 acquires image data for a plurality of pixels corresponding to an image of object 110. That is, each pixel includes image data for corresponding to a subdivision of the imaged portion of object 110 (and/or background to object 110).

Image acquisition system 140 and/or module 115 may include one or more components that are not illustrated in FIG. 1A. For example, one or more lenses, sunshades, broadband filters, apertures, or the like may be included in system 100 either prior to or after module 115.

Image acquisition system 140 may be in communication with a controller 150. Controller 150 may be integrated with image acquisition system 140, or may be separate. Controller 150 may be in communication with a processor 160 configured to process image data.

Controller 150 may control at least one of system 140, filter 120, and modifier 130. For example, controller may output signals to filter 120 that may cause filter 120 to move so that a different portion of filter 120 is aligned with modifier 130. Controller 150 may further cause system 140 to acquire data at the updated position of filter 120.

In some embodiments, controller 150 may comprise a computer device such as a personal computer to control image acquisition system 140, as well as one or more separate motor drive controllers (e.g., a stepper motor controller) for positioning filter 120 with respect to modifier 130. In such embodiments, processor 160 may be included in the computer device. The computer device may generate information to control motor drive controller(s), to control image acquisition system 140, to record image data, and to process image data.

Image information may be provided to processor 160. The image information may comprise, for example, information indicative of a light intensity (which is in turn indicative of reflectivity) at each of the wavelength bands for each of the image pixels.

Processor 160 may process image information to determine whether parameters of image acquisition system 140 are adequate. For example, as part of a set-up process, processor 160 may determine data indicative of a gain of image acquisition system 140 so that the brightest pixel is at the saturation limit of system 140. System 140 may be adjusted using controller 150 to have the determined gain.

A system such as system 100 of FIG. 1A may provide an additional advantage in that module 115 and image acquisition system 140 may be modular. That is, image acquisition system 140 may be a standard commercial imager, and a module 115 may be used without modifying the imager.

Figure 2:
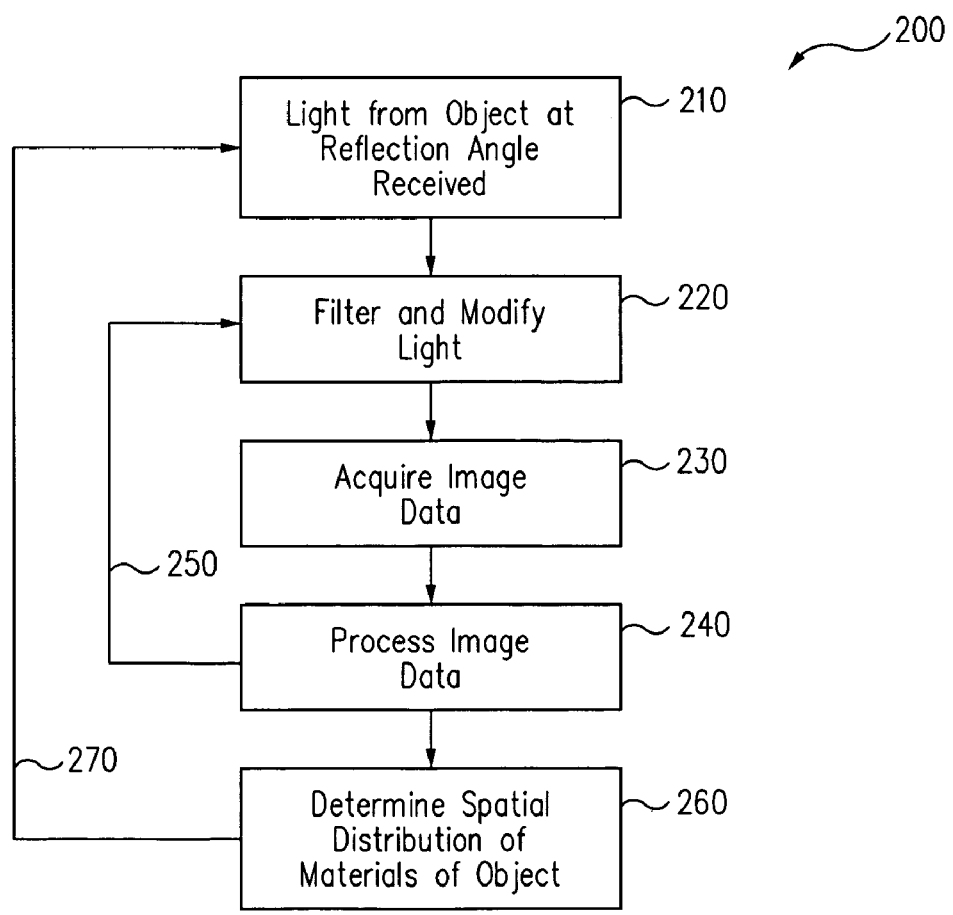
FIG. 2 is a flow chart of a method that may be used with a system such as that shown in FIG. 1A, according to some embodiments.

FIG. 2 is a flow chart of a method 200 that may be used with system 100 of FIGS. 1A to 1D, according to some embodiments.

At 210, light may be reflected from a portion of an object at a reflection angle, and received at a system such as system 100. At 220, the received light may be filtered and modified so that a particular wavelength band having a pre-selected bandwidth is transmitted to an image acquisition system. The filtered and modified light may be substantially one dimensional. At 230, image data may be acquired for a plurality of pixels, and processed at 240.

At 250, the system may be adjusted to acquire image data for a different wavelength band. At 220, received light may be filtered and modified so that the different wavelength band is transmitted to an image acquisition system, unless the data has been acquired for all wavelength bands of interest. Image data may again be acquired at 230, and processed at 240. At 260, one or more materials of the object may be identified based on processing the image data. For example, a spatial distribution of materials of the object may be determined based on the processing.

In some cases, there may be too much or too little light to adequately determine at least some of the materials of the object. For example, the received light corresponding to one or more of the image pixels may have too great an intensity, and the optical system may saturate. Thus, it may not be possible to accurately identify the material for those pixels. Similarly, for some pixels, the received light may have too little intensity. The signal may not be ascertainable above the noise to the extent necessary to determine the material for those pixels. For cases such as those, the reflection angle may be varied, and the process may be repeated, until sufficient data is acquired. Note that in some circumstances, accurate identification of a material for fewer than all pixels of an image may be sufficient.

Figure 3A:
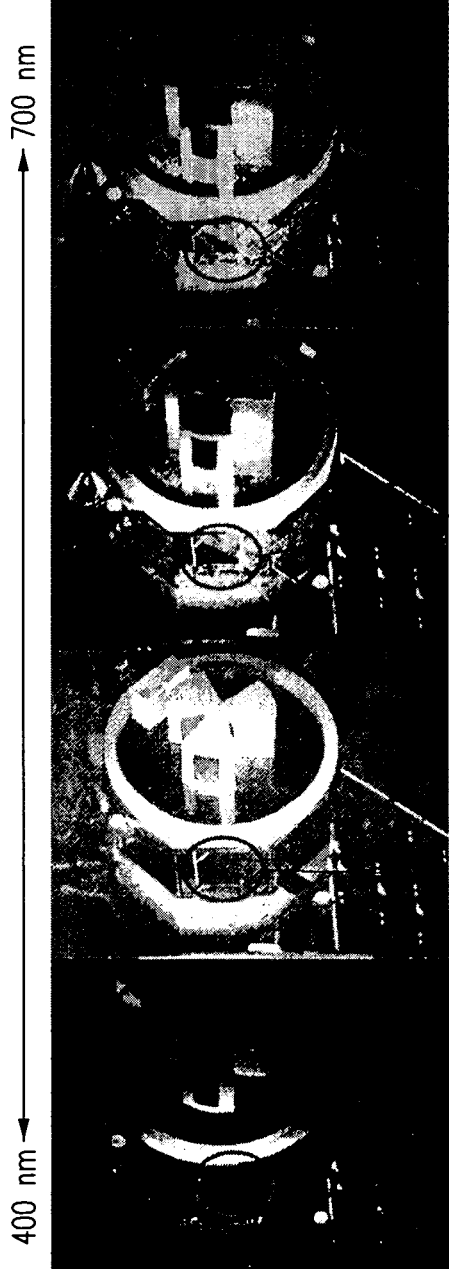
FIG. 3A is a greyscale representation of an image acquired at four different wavelength bands between 400 nm and 700 nm.
Figure 3B:
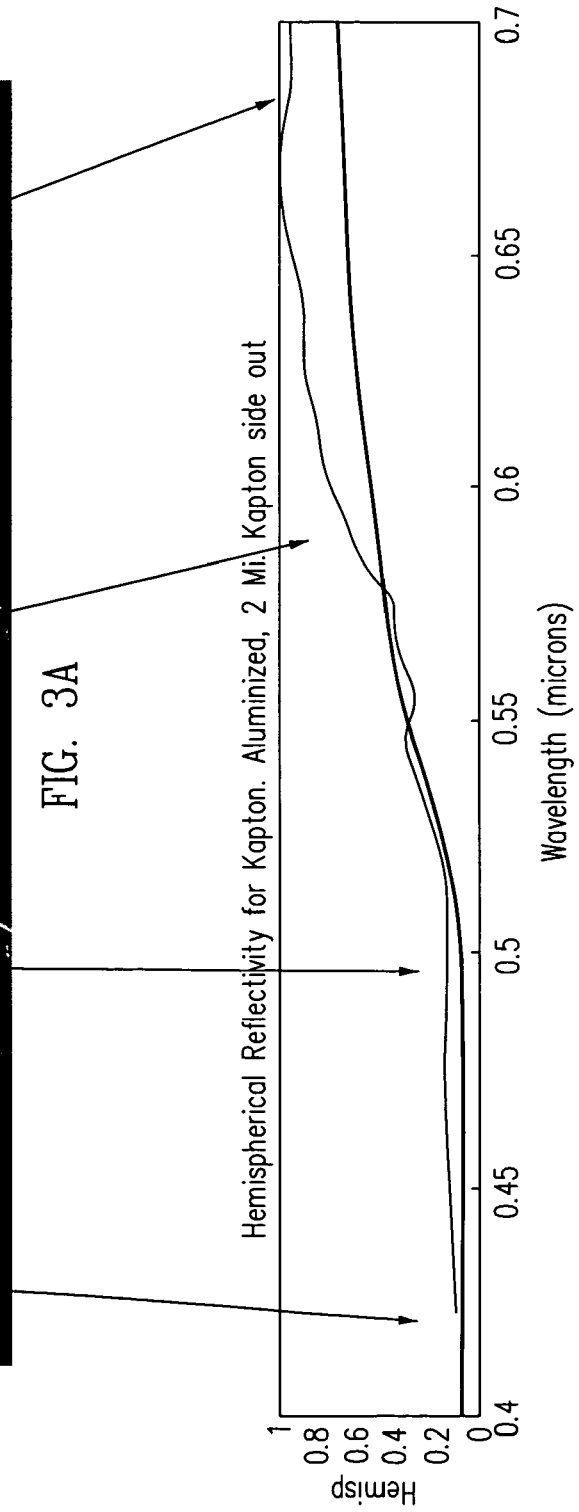
FIG. 3B is a corresponding graph of reflectivity versus wavelength for one pixel corresponding to a portion of the images shown in FIG. 3A.

FIG. 3A shows an image at four different wavelength bands between 400 nm and 700 nm. FIG. 3B shows a corresponding graph of reflectivity versus wavelength for one pixel of the image, where the pixel is located in the circled region of the image. Note that the images of FIG. 3A is a grey-scale representation of the response of the object to light corresponding to the different wavelengths. Note that each pixel in the image may have a different spectrum associate with the particular pixel.

Figure 4:
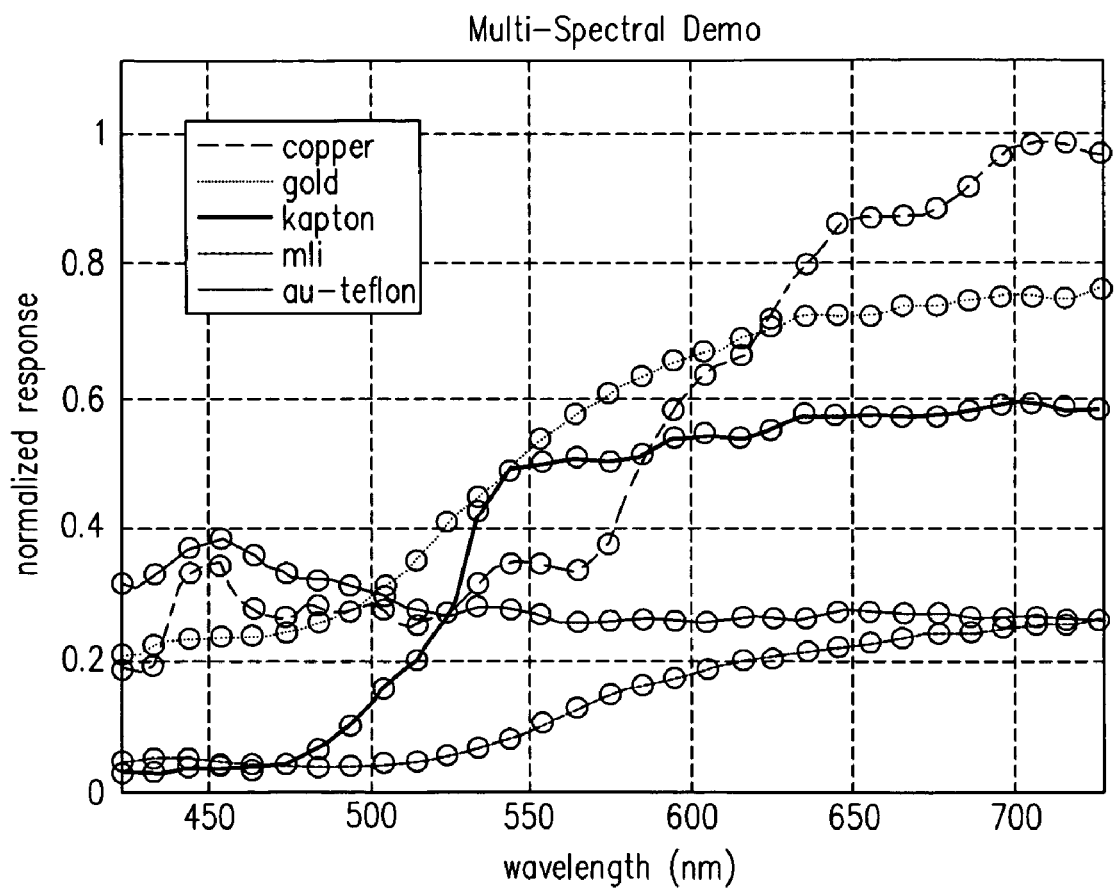
FIG. 4 is graph of reflectivity versus wavelength for a number of different candidate materials.

In order to determine the material or materials corresponding to the particular pixel of FIG. 3B, image data may be compared to data for a number of possible materials. FIG. 4 shows reflectivity versus wavelength for a number of different materials. The data used to generate FIG. 4 may be used to identify an unknown material from a plurality of candidate materials.

Material identification may be performed in a number of ways. For example, an error may be determined by comparing the difference between a measured reflectivity and a reference reflectivity, for each wavelength band and for a number of candidate materials. Equation (1) below illustrates a calculation of an error E for an m-th material, where n refers to one of the N wavelength bands. $R\_data_n$ refers to the measured reflectivity at the n-th wavelength band, while $R\_stored_{m,n}$ refers to the stored reflectivity for the m-th material at the n-th wavelength band.

$$E_m = \Sigma_N (R\_data_n - R\_stored_{m,n})^2 \quad \text{Equation (1)}$$

In some circumstances, using higher order curve-fitting may allow for more accurate material determination. For example, a score may be calculated for an m-th material by using a weighted combination of an error E such as that determined using Equation (1) above, and a first order error E' determined using a first order error calculation such as that illustrated by Equation (2) below. Equation (3) below shows determining a score Sm using both E and E', with weighting factors a and b, respectively.

$$E'_m = \sum_N \left( \frac{\delta R\_data(\lambda)}{\delta \lambda} \bigg|_{\lambda_n} - \frac{\delta Rstored(\lambda)}{\delta \lambda} \bigg|_{\lambda_n} \right)^2 \quad \text{Equation (2)}$$

$$S_m = aE_m + bE'_m \quad \text{Equation (3)}$$

In some embodiments, one or more correlation algorithms may be used to determine the identity of one or more materials. Correlation algorithms may compare optical parameters of the material to be identified with corresponding parameters of candidate materials. Correlation algorithms may determine, for example, a variance in a parameter X, $S^2_X$, a variance in a parameter Y, $S^2_Y$, a covariance of X with Y, $S^2_{XY}$, and a correlation coefficient r, as outlined in Equations (4) to (7) below.

$$S^2_X = \frac{\sum X^2}{N} - \frac{(\sum X)^2}{N^2} \quad \text{Equation (4)}$$

$$S^2_Y = \frac{\sum Y^2}{N} - \frac{(\sum Y^2)}{N^2} \quad \text{Equation (5)}$$

$$S^2_{XY} = \frac{\sum XY}{N} - \frac{\sum X \sum Y}{N^2} \quad \text{Equation (6)}$$

$$r = \frac{S^2_{XY}}{\sqrt{(S^2_X - S^2_Y)}} \quad \text{Equation (7)}$$

Figure 5:
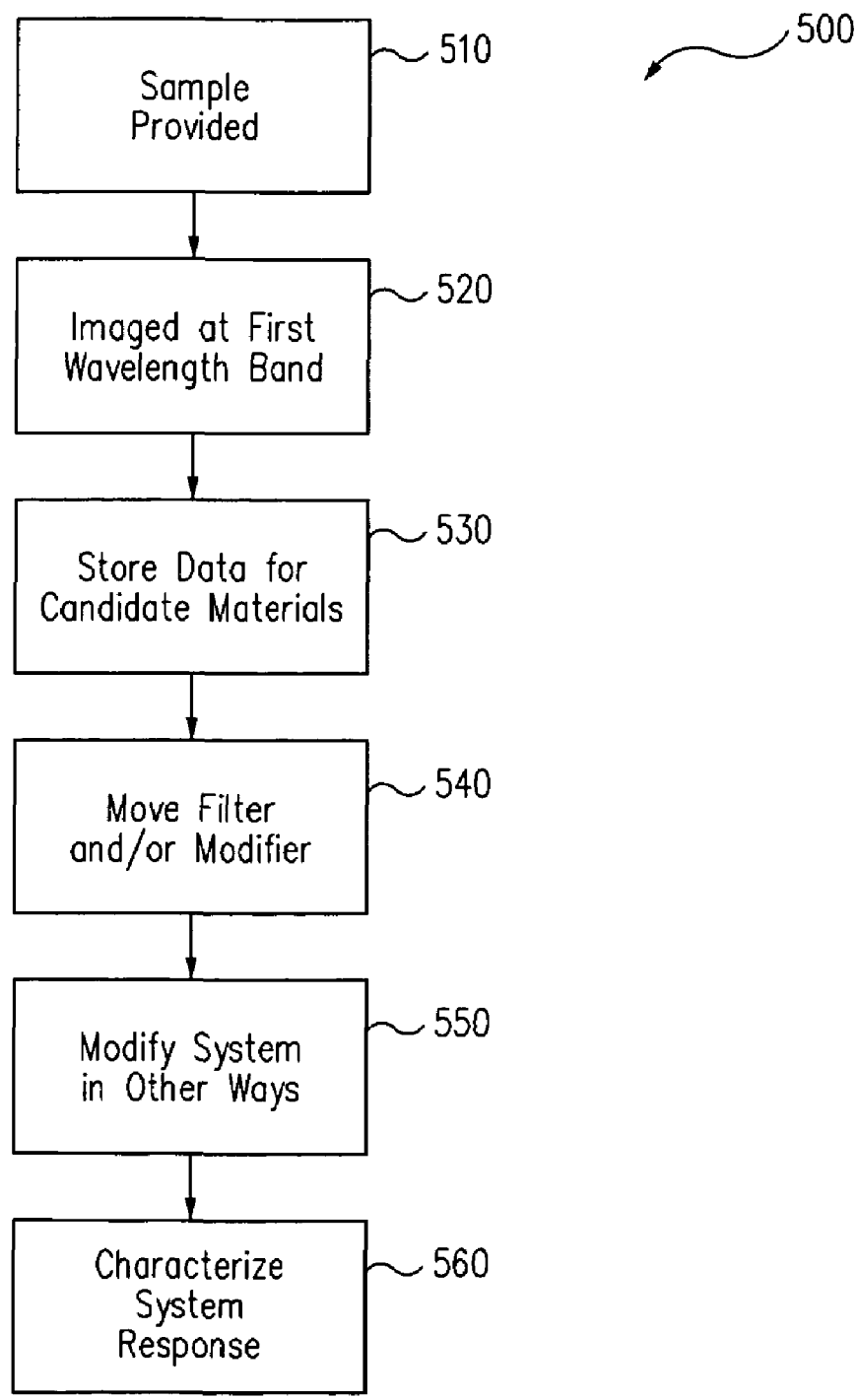
FIG. 5 is a flow chart of a method that may be used to train a system such as that shown in FIG. 1A.

Because the optical response of different systems under different conditions differs, in some implementations a system may be trained prior to being used to identify one or more materials of an object. FIG. 5 shows a method 500 that may be used to train a system such as that shown in FIG. 1A.

At 510, a sample comprising one or more known, candidate materials is provided. At 520, the sample is imaged at a first wavelength band using a system such as FIG. 1A, to acquire image data of a plurality of pixels corresponding to the sample, where the identity of the material(s) corresponding to different pixel sets is known. For example, the sample may include a copper region, an aluminum region, a Kapton™ region, and the like. At 530, data corresponding to pixels corresponding to each candidate material is stored for the first wavelength band. At 540, the filter and/or modifier is moved so that a different wavelength band is received in the image acquisition system, and the process is repeated. At 550, the system may be modified in other ways, and the process may be repeated for each of the wavelength bands. For example, an intensity of a light used to illuminate the sample may be changed, a magnification may be changed, a reflection angle may be changed, one or more electronic parameters (such as a gain) may be modified, and/or other modification may be made.

At 560, the acquired data may then be used to characterize the system response to each of the candidate materials, and subsequently used to identify the candidate materials in an acquired image to identify one or more materials. The system may also record a response to a region known to be "white," in order to derive a system spectral response. Alternately, the system may be calibrated before use, or it could use an alternate algorithm to derive the system spectral response, such as an algorithm using that the brightest pixel at each wavelength is equivalent to "white."

Figure 6:
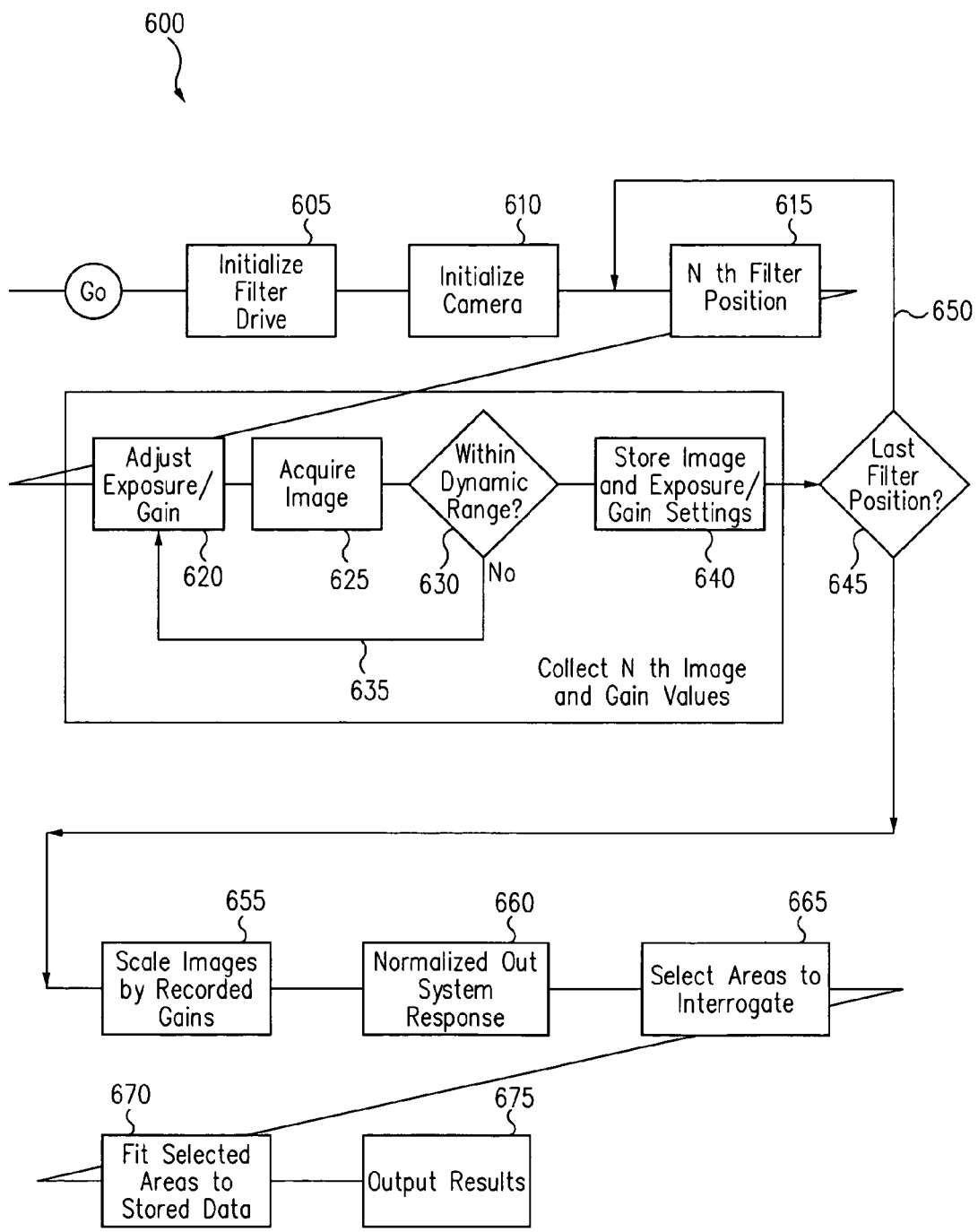
FIG. 6 is a flow chart of a method that may be used for setting up a system such as the system of FIG. 1A, acquiring data, and generating results, according to some embodiments.

Once a system such as system 100 of FIG. 1 is to be used to analyze the materials of an object, a setup process may be performed prior to acquiring image data. FIG. 6 shows a process 600 for setting up a system, acquiring data, and generating results.

At 605, a filter drive may be initialized. For example, a stepper motor controller may initialize a stepper motor to position the filter at a beginning position, prior to obtaining image data. At 610, an image acquisition system such as a camera may be initialized. At 615, the filter may be positioned at the Nth filter position (e.g., the first position corresponding to a first desired wavelength band). At 620, the exposure, gain, and/or other system parameters may be adjusted to first level(s). The first levels may be selected to be the levels expected to yield acceptable results under the imaging conditions.

At 625, an image may be acquired using the first levels of the system parameters. At 630, the image data may be analyzed to determine whether the image is within the dynamic range of the system. If it is not (e.g., parts of the image are saturated, or the gain is insufficient to obtain a desired signal to noise ratio), one or more system parameters may be adjusted at 635, and the process repeated.

Once the system parameters are adequate, the system parameter settings and the acquired image are stored at 640. At 645, the system determines whether the previous filter position was the last filter position. If not, the filter is adjusted to the next filter position at 650, and the process is repeated until data has been acquired at the last filter position.

At 655, the images may be scaled; for example, by recorded gains. At 660, the system response may be normalized. At 665, particular regions of the image data may be selected to interrogate. At 670, the data for the selected areas may be fit to stored data (e.g., correlated with stored spectra), and at 675 results may be output.

As noted above, systems and techniques provided herein may be used in a number of applications. One application is the identification of materials and/or material properties in space. Optical systems deployed on spacecraft generally need to be lightweight, reliable, and to operate without human intervention. A system such as that shown in FIG. 1A may provide sufficient data for material identification, without excessive weight. Other applications include factory inspection, contamination identification, and other applications where the material attributes can be distinguished by machine color that would be difficult to distinguish in a 3-color TV system.

In implementations, the above described techniques and their variations may be implemented as computer software instructions. Such instructions may be stored on one or more machine-readable storage media or devices and are executed by, e.g., one or more computer processors, or cause the machine, to perform the described functions and operations.

A number of implementations have been described. Nevertheless, it will be understood that various modifications may be made without departing from the spirit and scope of the invention. For example, additional, fewer, and/or different elements may be used to implement the invention. The order of elements in the apparatus and/or the order of acts performed may be different than that described above (e.g., the received light may be modified prior to being filtered, etc.). In another example, the filter may move, or the modifier may move, or both may move, in order to couple different wavelength bands into the image acquisition system. Further, elements illustrated as separate may be separate or may be integrated with other elements. Also, only those claims which use the words "means for" are intended to be interpreted under 35 USC 112, sixth paragraph. Moreover, no limitations from the specification are intended to be read into any claims, unless those limitations are expressly included in the claims. Accordingly, other implementations are within the scope of the following claims.

What is claimed is:

1. A method comprising:
   receiving light from an object comprising one or more materials at a multi-spectral optical module;
   at the multi-spectral optical module, sequentially transmitting a plurality of wavelength band portions of the received light, wherein the wavelength band portions each have a pre-selected bandwidth between about two nanometers and about forty nanometers, wherein transmitting each of the portions comprises:
      configuring a variable filter of the multi-spectral optical module to transmit light included in the associated wavelength band portion of the received light and to exclude light outside the associated wavelength band portion of the received light,
      altering a spatial profile of the light included in the associated wavelength band portion of the received light using a light modifier, wherein the light modifier is configured to be moved relative to both the variable filter and an image acquisition system, and
      transmitting the light included in the associated wavelength band portion of the received light to an image acquisition system;
   receiving the wavelength band portions at the image acquisition system;
   generating image data corresponding to each of the wavelength band portions;
   processing at least some of the image data; and
   identifying at least one material of the one or more materials based on the processing at least some of the image data.

2. The method of claim 1, wherein the light modifier modifies the received light to be substantially one dimensional.

3. The method of claim 2, wherein modifying the received light to be substantially one dimensional comprises transmitting a portion of the received light through an elongate aperture.

4. The method of claim 1, wherein the filter is a variable linear filter.

5. The method of claim 1, wherein the filter is a variable circular filter.

6. The method of claim 1, wherein configuring the filter comprises positioning the filter with respect to the light modifier to transmit the light included in the associated wavelength band portion of the received light and to exclude the light outside the associated wavelength band portion.

7. The method of claim 1, wherein receiving light from an object comprising one or more materials comprises receiving light reflected at a first reflection angle, and further comprising:
   receiving different light at a second different reflection angle at the multi-spectral optical module;
   at the multi-spectral optical module, sequentially transmitting another plurality of wavelength band portions of the different received light, wherein the wavelength band portions of the different received light each have a pre-selected bandwidth between about two nanometers and about forty nanometers, wherein transmitting each of the portions of the different received light comprises:
      configuring the filter to transmit light included in the associated wavelength band portion of the different received light and to exclude light outside the associated wavelength band portion of the different received light,
      altering a spatial profile of the light included in the associated wavelength band portion of the different received light using the light modifier, and
      transmitting the light included in the associated wavelength band portion of the different received light to the image acquisition system;
   receiving the wavelength band portions of the different received light at the image acquisition system;
   generating image data corresponding to each of the wavelength band portions of the different received light;
   processing at least some of the image data corresponding to each of the wavelength band portions of the different received light; and
   identifying at least one material of the one or more materials based on the processing at least some of the image data corresponding to each of the wavelength band portions of the different received light.

8. The method of claim 1, wherein processing at least some of the image data comprises processing the at least some of the image data and corresponding data indicative of an optical response of a plurality of candidate materials using a correlation algorithm.

9. The method of claim 1, wherein processing at least some of the image data comprises determining a score based on at least one of a first derivative and a higher order derivative of the at least some of the image data with respect to wavelength.

10. The method of claim 1, wherein the pre-selected bandwidth is included in the range extending from about ten nanometers to about thirty nanometers.

11. A system, comprising:
   an image acquisition system;
   a multi-spectral optical module configured to receive light, and sequentially transmit a plurality of wavelength band portions of the received light to the image acquisition system, wherein the wavelength band portions each have a pre-selected bandwidth of between about two nanometers and about forty nanometers, wherein the multi-spectral optical module comprises:
- a variable filter configured to transmit light included in the associated wavelength band portions of the received light and exclude light outside the associated wavelength band portions of the received light, and
- a light modifier configured to alter the spatial profile of the light included in the associated wavelength band portions of the received light, and further configured to be moved relative to both the variable filter and the image acquisition system; and
- a controller configured to control the multi-spectral optical module to couple each of the plurality of wavelength bands to the image acquisition system in turn.

12. The system of claim 11, wherein the light modifier is configured to format the received light to transmit substantially one dimensional light to the image acquisition system.

13. The system of claim 12, wherein the light modifier comprises a light blocker-including an aperture.

14. The system of claim 11, wherein the variable filter is selected from the group consisting of a linear variable filter and an angular variable filter.

15. The system of claim 11, wherein the multi-spectral optical module is configured to transmit a particular one of the plurality of wavelength bands based on a relative position of the filter with respect to the light modifier.

16. The system of claim 15, wherein the controller is configured to position at least the filter with respect to the light modifier to couple each of the plurality of wavelength bands to the image acquisition system in turn.

17. The system of claim 11, wherein the pre-selected bandwidth is between about ten nanometers and about thirty nanometers.

* * * * *